United States Patent [19]

Pleinis et al.

[11] Patent Number: 4,991,440

[45] Date of Patent: Feb. 12, 1991

[54] METHOD OF ULTRASONICALLY MEASURING THICKNESS AND CHARACTERISTICS OF ZIRCONIUM LINER COEXTRUDED WITH ZIRCONIUM TUBE

[75] Inventors: Michael J. Pleinis, Ogden; David M. Allen, Brigham City, both of Utah

[73] Assignee: Westinghouse Electric Corp., Pittsburgh, Pa.

[21] Appl. No.: 474,898

[22] Filed: Feb. 5, 1990

[51] Int. Cl.⁵ .................... G01B 17/02; G01N 29/00
[52] U.S. Cl. ............................... 73/615; 73/609; 73/612
[58] Field of Search ............... 73/597, 598, 622, 609, 73/610, 612, 613, 614, 611, 615

[56] References Cited

U.S. PATENT DOCUMENTS

| | | | |
|---|---|---|---|
| 3,169,393 | 2/1965 | Stebbins | 73/611 |
| 3,808,879 | 5/1974 | Rogers | 73/615 |
| 3,901,071 | 8/1975 | Hansen | 73/615 |
| 3,930,404 | 1/1976 | Ryden, Jr. | 73/622 |
| 3,986,389 | 10/1976 | Mesina et al. | 73/611 |
| 4,033,176 | 7/1977 | Eberie et al. | 73/611 |
| 4,123,943 | 11/1978 | Roddy et al. | 73/597 |
| 4,147,065 | 4/1979 | Lather et al. | 73/615 |
| 4,160,385 | 7/1979 | Gromlich et al. | 73/622 |
| 4,432,235 | 2/1984 | Renzel et al. | 73/610 |
| 4,669,310 | 6/1987 | Lester | 73/597 |
| 4,721,902 | 1/1988 | Tellerman et al. | 73/610 |
| 4,918,989 | 4/1990 | Desruelles et al. | 73/627 |

FOREIGN PATENT DOCUMENTS

| | | | |
|---|---|---|---|
| 142210 | 7/1985 | Japan | 73/609 |

*Primary Examiner*—Hezron E. Williams
*Assistant Examiner*—Rose M. Finley
*Attorney, Agent, or Firm*—Z. L. Dermer

[57] ABSTRACT

A coextruded zirconium tube and tube liner are monitored along their lengths by well known ultrasonic measurement techniques that are modified by the blocking out of extraneous signals at opposite sides of a timing gate that varies in width according to variations in the width and shape characteristics of successive points along the length of such coextruded tube and liner. The blocking of such extraneous signals enables a normally very weak signal representing the interface between tube and tube liner to be identified and used, together with a group of stronger signals representing the inner surface of the tube liner, in monitoring tube liner thickness and characteristics by a sonic wave traversing the distance across the timing gate.

6 Claims, 2 Drawing Sheets

METHOD OF ULTRASONICALLY MEASURING THICKNESS AND CHARACTERISTICS OF ZIRCONIUM LINER COEXTRUDED WITH ZIRCONIUM TUBE

BACKGROUND OF THE INVENTION

1. Field of the Invention

The invention has to do with methods for ultrasonically determining thickness and characterstics of an interior part at various points along the length of a coextending outer part.

2. Description of the Prior Art

Ultrasonic measuring of the type here concerned is old and well known. Transducer and transceiver instrumentation for accomplishing such measuring can be purchased commercially. Accessory instrumentation for blocking out certain unwanted signals is available for use with the transceiver and provision is made for plugging in a strip chart recorder so thicknesses and characteristics of the interior part can be visually observed and the chart can be kept as a permanent record. Moreover, it is common for the transceiver to be equipped with a cathode ray tube (CRT) so that the signals can be displayed as they are received. However, in instances in which strength differences between diverse signals are very great, with the one critical signal being very weak and others being very strong, interference by extraneous signals can become so diffuse and pervasive as to destroy the taking of any effective measurements.

Such a situation has heretofore prevented the use of this otherwise common ultrasonic technique for monitoring an ultrasonic signal from the interface between an extruded tube of zirconium metal and a coextruded tubular liner of a very similar zirconium metal and similarly monitoring an ultrasonic signal from the interior surface of the lined tube, from which signals thicknesses and characteristics of the liner are calculated within the instrumentation, and provided as output, based on timing the travel of the ultrasonic wave between such signals, all in customary manner.

It is important in the nuclear energy industry utilizing such coextruded zirconium tubes for containing nuclear fuel that the thickness of the liner be substantially uniform along the length of the tube and that measuring such thickness be possible short of destruction of the tube by cutting through it at intervals. Utilizing well known ultrasonic techniques would be a solution but has heretofore been regarded as impossible from a practical standpoint.

SUMMARY OF THE INVENTION

A primary objective in the making of the present invention was to provide a method by which essentially known ultrasonic signal producing and monitoring apparatus can be used to obtain useful measurements of liner thicknesses and characteristics along the length of a zirconium metal tube coextruded with a zirconium metal liner.

In accordance with the invention, the very weak ultrasonic signal representing the interface between tube and liner is protected from loss among overriding extraneous signals by blocking out such extraneous signals at both sides of the timing gate between the critical signals and preferably also within the span of the timing gate between such critical signals, thereby maintaining a useable signal to noise ratio which permits tracking and measurement of such weak signal while the ultrasonic transducer and tube are in motion relative to each other. This is accomplished by installing signal blocking gates spanning strategic areas, rather than just a single area afforded by the usual blocking gate accessory that is commercially available. The usual timing gate is provided for measuring the time taken for the ultrasonic wave to pass from the liner interface to the inner surface of the lined tube.

A feature of preferred embodiments of the invention is providing a blocking gate for extraneous signals that may invade the timing area. In interpreting the strip chart recording, transient noise signals of very short duration that occur at random and appear as "spikes" are irrelevant and are to be ignored. This can be accomplished by computer analysis if the equipment is computerized.

BRIEF DESCRIPTION OF THE DRAWINGS

The best mode presently contemplated for carrying out the invention in actual practice is illustrated in the accompanying drawings, in which.

DETAILED DESCRIPTION OF THE ILLUSTRATED EMBODIMENT

Figure 1:
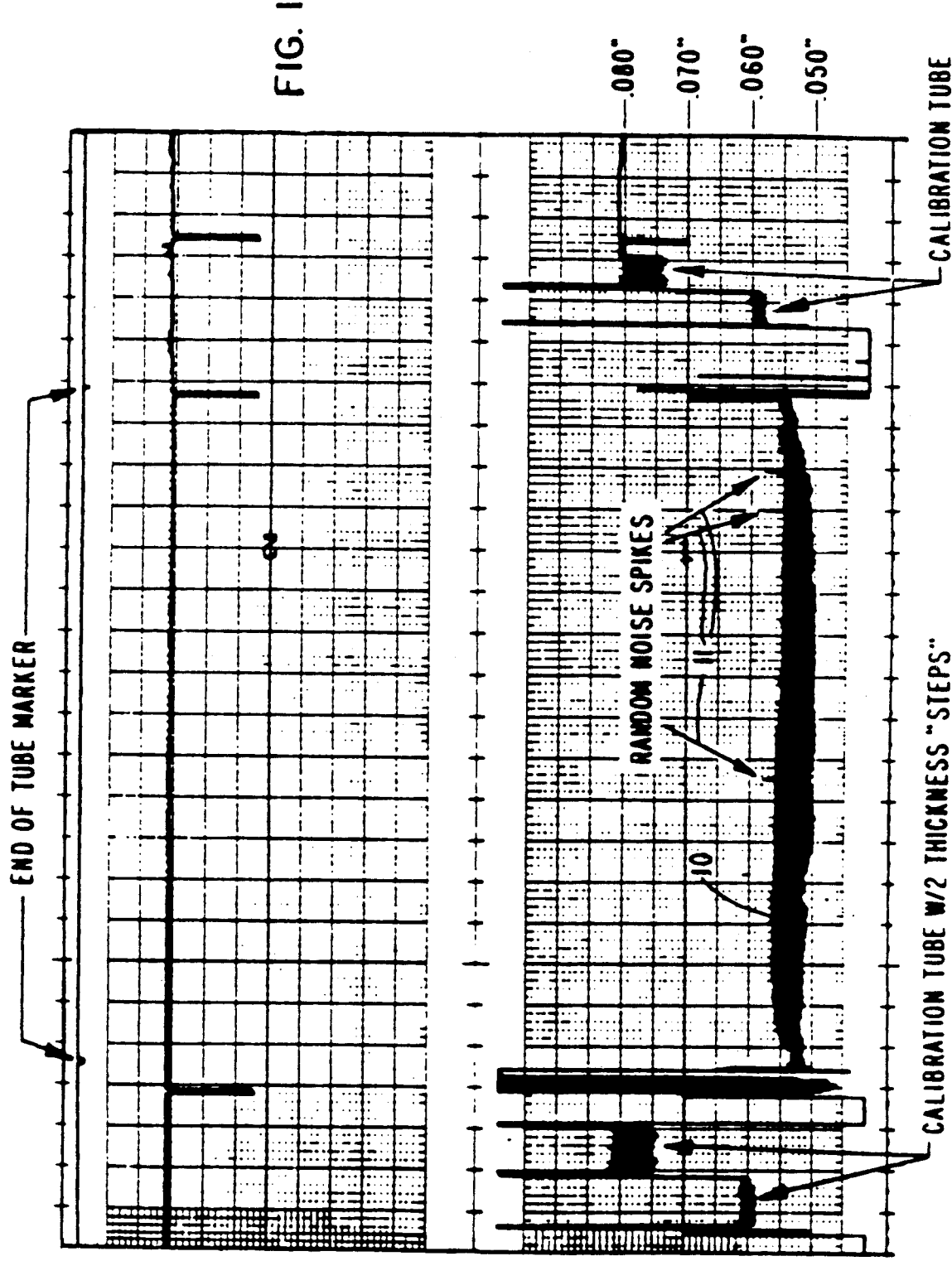
FIG. 1 is a full face representation somewhat enlarged of a typical strip chart recording obtained by use of the method of the invention showing thicknesses and varying characteristics of a zirconium metal tube liner along the length of a lined zirconium metal tube.

The best mode presently contemplated for carrying out the invention is to employ a wheeled carriage (not shown) known in the art, for holding a gimble-mounted, ultrasonic transducer and for riding on and along the tube so as to maintain the critical geometric relationship between transducer and liner-tube interface. Since tubes of the type concerned are not perfectly cylindrical, being slightly bowed at various points along their lengths, the carriage is preferably provided with springs at strategic locations so as to absorb jolting due to the uneven rotation of the tube.

Ultrasonic transducers, ultrasonic detectors, and blinding gate accessories are available commercially. Their use is well known to those skilled in the art, so it is unnecessary to describe them in detail.

In the present instance, a six inch focal length, point focused, ten MHz ultrasonic tranducer, e.g. the one made by Ultran Laboratories Inc. of State College, Pennsylvania, and sold commercially under the trade designation MS75, and an ultrasonic flaw detector, e.g. the one formerly made by Sonic Instruments Inc., now Stavely NDT Technologies, Inc., Kennewick, Washington, and sold commercially under the trade designation Sonic FTS Mark VI, have been found to perform very satisfactorily and are preferred for use in carrying out the method of the invention. The detector comes with a single blocking gate and is modified by the addition of two other signal blocking gates to filter high frequency noise transients and to keep unwanted signals, of longer duration than the wanted signals, form interfering.

The signal blocking instrumentation is constructed and arranged to block extraneous ultrasonic signals occurring throughout distances at opposite sides of the very weak signal that is representative of the interface between the tube and its liner. Such distances extend at least between such interface and the inner cylindrical surface of the coextruded tubular product, which inner surface gives a relatively strong signal, and between such interface and the outer cylindrical surface of the coextruded tubular product, which outer surface also gives a relatively strong signal. The signal blocking instrumentation is also constructed and arranged to block all noise from the hollow interior of the tube as viewed on the CRT of the detector.

Required blocking instrumentation is available commercially, e.g. as made by the aforesaid Sonic Instruments Inc. and sold under the trade designation VTA063A Main Blocking Gate. The Sonic FTS Mark VI comes equipped with such main blocking gate. The other two blocking gates incorporated pursuant to the invention are added to accomplish the purposes of the invention.

Although blocking as described above enables the very weak signal arising from the liner-tube interface to be located and followed, the momentary, extraneous, transient noise signals mentioned above do appear at random and are to be ignored.

It should be realized that the zirconium tube and its zirconium liner are almost identical metals, the tube being the alloy known as Zircalloy 2 with a maximum of about 1.7% tin, 0.2% iron, 0.15% chromium, and 0.08% nickel and the liner being essentially pure zirconium. Heretofore, there has been no generally available way of non-destructively testing such coextruded zirconium metal tubes for unifomity of liner thickness, since the very weak sonic signal afforded by the tube-liner interface has precluded the use of customary ultrasonic measurement systems.

A typical strip chart recording made in accordance with the method of the invention and indicative of the thicknesses and characteristics of the coextruded tube liner along the length of the coextruded tube and liner is shown in FIG. 1 of the drawing, with the liner thicknesses represented by the positions of the curve 10 on the chart divisions. Each division of the recording chart paper represents 0.001 of an inch. Momemtary, extraneous, transient noise signals appear as "spikes" 11 and are ignored in reading the chart. A typical two-step, standard scan chart especially made for calibration purposes, as is customary in the art, appears in the lower part of the figure.

Figure 2:
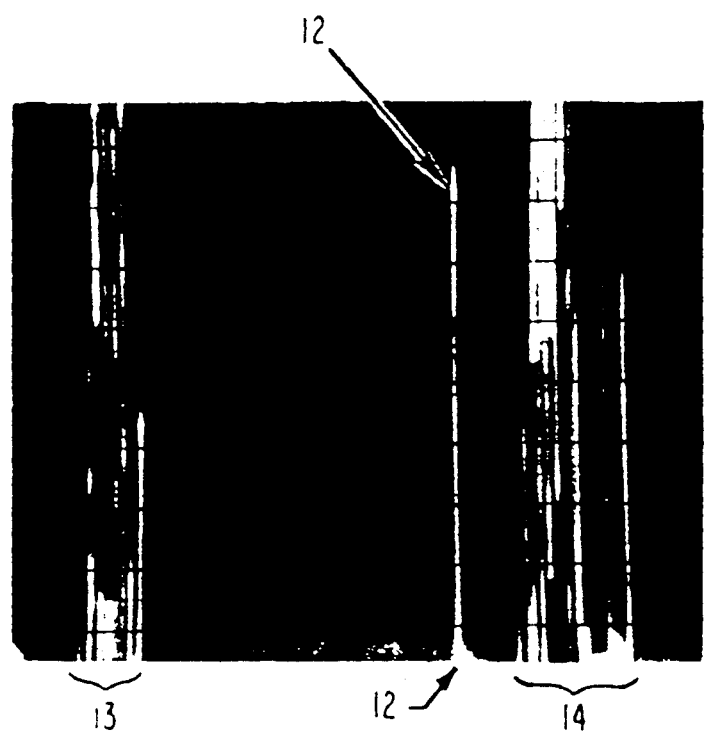
FIG. 2, a schematic representation of a CRT display of signals received from the ultrasonic measuring apparatus, with the liner interface echo signal identified as such and other signal areas similarly identified.

FIG. 2 represents a typical display by the CRT screen of the ultrasonic flaw detector instrument, with the liner interface echo signal 12 standing out clearly between a group of signals 13 representing the tube outside surface echo and a group of signals 14 representing the inside surface, i.e., the inside diameter (ID) echo.

Figure 3:
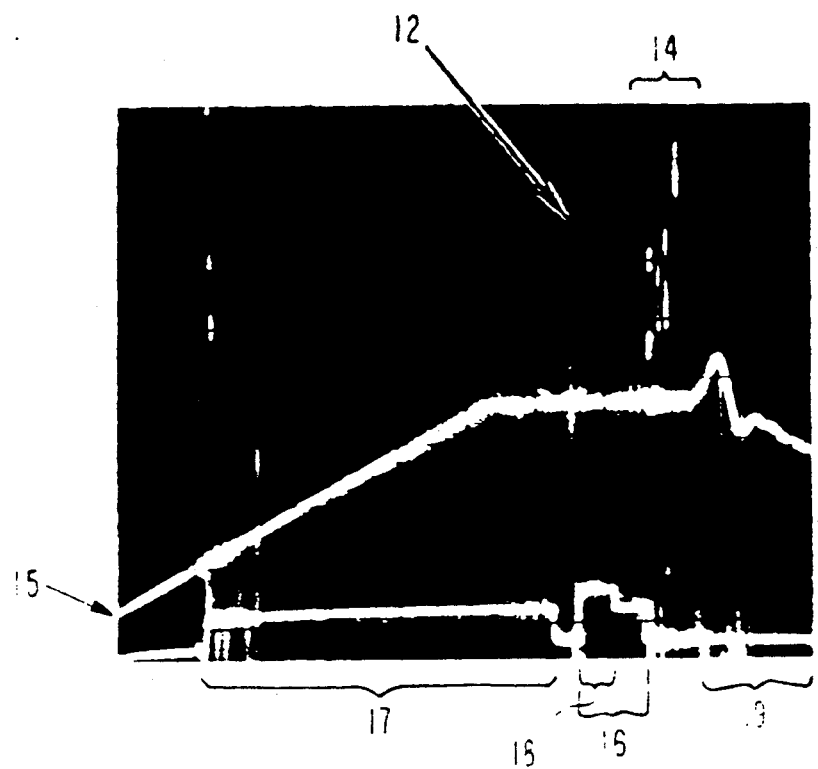
FIG. 3, a similar schematic representation showing the liner interface signal, a distance, amplitude, correction (DAC) curve, the timing gate, and blocking gates.

FIG. 3 represents a similar display including a distance, amplitude, correction (DAC) curve 15, preferably produced by Sonic Instruments Inc's CDO 68 Micro-Dec module, and showing liner interface signal 12, a timing gate 16, a main blocking gate 17, a second blocking gate 18, and a third blocking gate 19.

Timing gate 16 varies in width according to the elapsed time for the sonic wave to travel from the tube-liner interface 12 to the inner surface of the lined tube and controls the pen of the strip chart recorder. The recorded curve 10 is truly representative of the sonic wave that measures the thicknesses of the tube liner, the thickness of the tube liner at any point along its length being indicated by the location of curve 10 on the chart recording. The width of the recorded curve 10 represents the eccentricity of the cross-section of the liner tube at any given point, the wider the curve the greater the eccentricity of the liner cross-section.

Main blocking gate 17, whose right boundary is adjustable to make room for signal 12, blocks out strong signals on the left in FIG. 3 that would overpower and render indistinct tube-liner interface signal 12, and blocking gate 19 does the same to the right of timing gate 16 in FIG. 3. Blocking bate 19, whose left boundary is adjustable to make room for signals 14, blocks out signals whose durations are less than a given time in milleseconds, e.g. two or three milleseconds.

The left and right boundaries of timing gates 16 are free to float, so that the left edge of curve 10 will represent a minimum thickness value of the tube liner and the right edge will represent a maximum thickness value, thereby enabling the specifying of minimum and maximum thickness values to potential customers for the product. The distance between signal 12 and the group of signals 14 is the measure of tube liner thickness.

Blocking gate 18 must be kept narrower than timing gate 16 while covering as large an area as possible. Its left boundary is locked onto signal 12 and its right boundary is kept well within timing gate 16 by manual adjustment of the equipment based on visual observation of the changing width of timing gate 16 appearing as an illuminated rectangle on the CRT screen.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim as our invention:

1. A method of measuring wall thicknesses and cross-sectional characteristics of a zirconium metal liner of a coextruded zirconium metal tube and tube liner along the length of the coextrusion, comprising continously applying ultrasonic energy to the outer surface of a rotating coextruded tube and the tube liner while traveling along the length of said tube and tube liner, so as to generate echo signals corresponding, respectively, to the interface between said tube and tube liner and the inside surface of coextruded tube and tube liner; detecting a weak ultrasonic echo from said interface between the tube and liner and a stronger ultrasonic echo from said inside surface of said coextruded tube and tube liner to define a variable timing zone therebetween corresponding to the thickness and cross-sectional characteristics of said tube liner at successive points along the travel of application of ultrasonic energy while blocking out extraneous signals at opposite sides of and within said timing zone by respective blocking gates; locking the side of the blocking gate that is within said timing zone and adjacent to the detected interface echo signal onto said interface echo signal; adjusting the opposite side of said blocking gate from time to time so that said blocking gate will cover a maximum area of said timing zone while still being narrower than said timing zone; repeatedly timing travel of an ultrasonic wave across said timing zone along said length of the coextrusion; and determining liner thicknesses and characteristics from the measured travel times of the ultrasonic wave.

2. A method according to claim 1, wherein the detected ultrasonic echo from the interface and at the inside surface of the coextruded tube and liner are depicted on a CRT screen along with the ultrasonic energy reflected that from the tube outer surface.

3. A method according to claim 2, wherein a DAC curve, the timing zone, and the blocking gates are also depicted on the CRT screen.

4. A method according to claim 1, wherein a curve delineating tube liner thicknesses and characteristics is depicted on a strip chart recording by a strip chart recorder whose pen is controlled by ultrasonic energy derived from the timing zone.

5. A method according to claim 1, wherein any momentary transient noise signals that are not blocked by the blocking gates are ignored as irrelevant.

6. A method according to claim 1, wherein the tube is a zirconium alloy and the liner is substantially pure zirconium.

* * * * *